US009155709B1

(12) United States Patent
House, Sr. et al.

(10) Patent No.: US 9,155,709 B1
(45) Date of Patent: Oct. 13, 2015

(54) BUFFERED HYDROALCOHOLIC POVIDONE IODINE COMPOSITION AND METHOD

(71) Applicants: Hugh A. House, Sr., Wenonah, NJ (US); Edward A. House, Sr., Wenonah, NJ (US)

(72) Inventors: Hugh A. House, Sr., Wenonah, NJ (US); Edward A. House, Sr., Wenonah, NJ (US)

(*) Notice: Subject to any disclaimer, the term of this patent is extended or adjusted under 35 U.S.C. 154(b) by 0 days.

(21) Appl. No.: 14/540,605

(22) Filed: Nov. 13, 2014

(51) Int. Cl.
| | | |
|---|---|---|
| *C11D 3/00* | (2006.01) | |
| *A61K 9/70* | (2006.01) | |
| *A61K 31/79* | (2006.01) | |
| *A61K 47/10* | (2006.01) | |
| *A61K 31/167* | (2006.01) | |
| *A61K 47/18* | (2006.01) | |
| *A61K 31/235* | (2006.01) | |

(52) U.S. Cl.
CPC ............. *A61K 9/7015* (2013.01); *A61K 31/167* (2013.01); *A61K 31/235* (2013.01); *A61K 31/79* (2013.01); *A61K 47/10* (2013.01); *A61K 47/186* (2013.01)

(58) Field of Classification Search
None
See application file for complete search history.

(56) References Cited

U.S. PATENT DOCUMENTS

| | | | |
|---|---|---|---|
| 2,706,701 A | 4/1955 | Beller | 167/70 |
| 2,900,305 A | 8/1959 | Siggia | 167/70 |
| 4,151,275 A | 4/1979 | Cantor et al. | 424/78.07 |
| 5,081,158 A | 1/1992 | Pomerantz | 514/781 |
| 5,137,718 A | 8/1992 | Gillespie | 424/78.24 |
| 5,716,611 A | 2/1998 | Oshlack et al. | 424/78.25 |
| 5,916,882 A | 6/1999 | Jeng | 514/57 |
| 2005/0282727 A1* | 12/2005 | Shapiro | 510/504 |

FOREIGN PATENT DOCUMENTS

NL 1016776 C2 * 6/2002

OTHER PUBLICATIONS

English Translation of NL 1016776 C2 to Caussin dated Jun. 4, 2002, pp. 1-20.*
Article from the website: http://gateway.nlm.nih.gov entitled "Efficacy and safety of a quick drying rubbing type povidone-iodine alcoholic disinfectant solution." Kirita T, Hamano K, Ochi T, Ihara H, Nishiyama T, Seshimo A, Yagi Y, Sakakida K.; *Postgrad Med J.* 1993; 69 Suppl 3:S27-32; two (2) pages.
Article from the website: http://findarticles.com entitled "Chlorhexidine vs. Povidone-Iodine Skin Antisepsis for Blood Culture"; American Family Physician, Apr. 1, 2000 by Richard Sadovsky; three (3) pages.
Article from the website: http://www.sciencedirect.com entitled "Comparison of povidone-iodine solution and soft white paraffin ointment in the management of skeletal pin-sites: A pilot study"; Journal of Orthopaedic Nursing, vol. 9, Issue 4, Nov. 2005, pp. 218-225; two (2) pages.
Article from the website: http://archderm.ama-assn.org entitled "A new in vivo model for the evaluation of topical antiseptics on superficial wounds. The effect of 70% alcohol and povidone-iodine solution"; Archives of Dermatology, vol. 120 No. 1, Jan. 1984; P.M Mertz, O.M. Alvarez, R.V. Smerbeck and W.H. Eaglstein; one (1) page.
Article from the website: http://www.annals.org entitled "Chlorhexidine Compared with Povidone-Iodine Solution for Vascular Catheter-Site Care"; A Meta-Analysis; Nathorn Chaiyakunapruk, PharmD, PhD: David L. Veenstra, PharmD, PhD: Benjamin A. Lipsky, MD; and Sanjay Saint, MD, MPH; Jun. 4, 2002, vol. 136, Issue 11, pp. 792-801; eleven (11) pages.
Article from the website: http://www.medscape.com entitled "Alcoholic Povidone-Iodine More Effective Than Aqueous", Medscape Medical News, Laurie Barclay, MD Apr. 6, 2004, two (2) pages.
CAS Registry No. 56-81-5 (Nov. 16, 1984).
Fujisawa et al. Enthalpies of dilution of mono-,di- and poly-alcohols in dilute aqueous solutions at 298.15 K. Journal of Thermal Analysis and Calorimetry (2002); 69: 841-848.
CAS Registry No. 7558-79-4 (Nov. 16, 1984).
A label from equaline$_{TM}$ for topical antiseptic solution, distributed by Albertsons, Inc. of Boise Idaho, Expiration Date Jun. 2010.
Technical Bulletin for "Isopropyl Alcohol ExCel$_{AP}$® Povidone-Iodine" manufactured by Aplicare, Inc.; undated.
A website print out from solutionsonline.us showing "Viroxyn®"; undated.
PVP-Iodine Antiseptic Brochure, International Specialty Products 2004.
Kutarski et al. To dry or not to dry? An assessment of the possible degradation in efficiency of preoperative skin preparation caused by wiping skin dry. Annals of the Royal College of Surgeons of England 1993; 75:181-185.
Betadine MSDS. Betadine® Solution (10% povidone iodine) Material Safety Data Sheet. Purdue Products LP (Jul. 14, 2005).
Betadine Package Insert. Betadine®(povidone iodine) Solution. Alcon Laboratories, Inc. (Feb. 2006).

* cited by examiner

*Primary Examiner* — Robert A Wax
*Assistant Examiner* — Randeep Singh
(74) *Attorney, Agent, or Firm* — Blake P. Hurt; Tuggle Duggins P.A.

(57) ABSTRACT

A composition containing two (2) essential medicaments formed in situ, hydroalcoholic povidone iodine and hydroalcoholic benzalkonium chloroiodide after mixing a stock solution and a topical reacting solution which form a safe and effective antiseptic, antimicrobial protective polymeric film after topical application to the skin. A method of preparing a composition for forming a protective polymeric film after topical application includes mixing povidone iodine in a buffer solution to form a stock solution and mixing that solution on a one to one basis with a topical reacting solution with a hydroalcoholic benzalkonium chloride with lidocaine or benzocaine solution. A related method of treating injured or diseased skin is also disclosed.

14 Claims, 1 Drawing Sheet

BUFFERED HYDROALCOHOLIC POVIDONE IODINE COMPOSITION AND METHOD

FIELD OF THE INVENTION

The invention disclosed herein pertains to an antimicrobial povidone iodine (PI) composition, and more particularly to an antimicrobial buffered hydroalcoholic povidone iodine complex formulation effective for a variety of uses including forming a medicated protective polymerized film (bandage) when applied to an area of skin for sustained topical skin care and treatment of diseases which is dry to the touch and is water soluble.

DESCRIPTION OF THE PRIOR ART AND OBJECTIONS OF THE INVENTION

Povidone Iodine (PI) solutions are well-known for their antiseptic properties. U.S. Pat. No. 5,716,611 to Oshlack et al. discloses an anti-microbial formulation for cleansing the skin that alleviates skin irritation often associated with topical PI application. The Oshlack et al. formulation comprises povidone iodine, ethoxylated higher aliphatic alcohol and an ethoxylated cholesterol derivative. The Oshlack et al. patent provides an anti-microbial formulation for cleansing the skin. U.S. Pat. No. 5,081,158 to Pomerantz provides a waterproof medicated protective cellulosic "physical film" which can be applied for in situ treatment of body tissues but does not form a polymerized film for sustained protection. Alcon Laboratories, Inc. provides a BETADINE (povidone iodine) solution (BETADINE® 5% Sterile Ophthalmic Prep Solution, product sheet revised 02/2006) which includes a pyrrolidinone polymer for use on the eye such as on the ocular surfaces, but such is not film forming for sustained protection. U.S. Pat. No. 4,151,275 to Cantor et al. discloses an iodine tincture which provides antimicrobial properties however this product also does not provide film forming capabilities. Caussin NL 1016776C2; issued 4 Jun. 2002 discloses compositions containing PI, an Iodophor, and Lidocaine as a local anesthetic for use in treating burns, scrapes and abrasions. Products disclosed in this invention specifically exclude alcohol as an antiseptic/bactericide and discount benzalkonium chloride as a viricide/fungicide.

Current medical treatments such as the compositions disclosed above and other PI solutions which are utilized for topical skin treatment do not provide a composition which can be applied to the skin and thereafter forms an effective, protective film barrier (bandage) which releases medicament for various skin treatments to aid in healing the skin where minor wounds and specific diseases are present. With the increase in various skin afflictions such as minor abrasions, cuts, burns, infections, fungus, viruses and other ailments and specific diseases, there exists a great need for providing an instant protective film barrier (bandage) having capabilities of releasing medicine to the infected area.

Therefore, an objective of the present invention is to provide an antimicrobial, viricidal and fungicidal substance with benzalkonium chloroiodide formed in situ in a buffered hydroalcoholic povidone iodine complex formulation that produces a protective polymerized film layer (bandage) for topical skin care and application.

Another objective of the present invention is to provide an antimicrobial buffered hydroalcoholic povidone iodine complex formulation that provides a sustained released source of benzalkonium chloroiodide at the site of topical application.

Still another objective of the present invention is to provide an antimicrobial buffered hydroalcoholic povidone iodine complex formulation that provides a protective polymerized antimicrobial film at an area of topical application if sprayed on and left on the skin.

Yet another objective of the present invention is to provide an antimicrobial buffered hydroalcoholic povidone iodine complex formulation that provides a sustained released source of benzalkonium chloroiodide medicament for the topical treatment of infections such as MRSA, cellulitis, athletes' feet, jock itch, bed sores, acne, blemishes, full body antimicrobial cleansing and maintenance, body deodorant, PFB's (Pseudo-Folliculittis Barbae), cold sores, herpes simplex and many other skin conditions and diseases.

A further objective of the present invention is to provide an antimicrobial buffered hydroalcoholic povidone iodine complex formulation that can be used for water purification.

It is still a further objective of the present invention to provide an antimicrobial buffered hydroalcoholic povidone iodine complex formulation effective for controlling dog mange, flea and tick conditions.

It is yet another objective of the present invention to provide an antimicrobial buffered hydroalcoholic povidone iodine complex formulation effective for the treatment of fish aquariums.

It is still a further objective of the present invention to provide an antimicrobial buffered hydroalcoholic povidone iodine complex formulation effective in unit dose packages for emergency iodine therapy to protect the thyroid gland before and after radiation exposure. Various other objectives and advantages of the present invention will become apparent to those skilled in the art as a more detailed description is set forth below.

SUMMARY OF THE INVENTION

The aforesaid and other objectives are realized by providing a composition which will form a polymerized film upon topical application and will provide a sustained released source of medicament at the site of topical application. The composition includes a stock solution (Table 1) and a topical reacting solution (Table 4). In the preferred embodiment of the invention, the stock solution is a buffered ten percent (10%) by weight povidone iodine solution and the topical reacting solution contains a hydroalcoholic weight percent of at least about 90-99%, preferably 93-95%, a benzalkonium chloride weight percent of at least about 0.005-0.130%, preferably 0.125-0.130%, and a lidocaine weight percent of least about 1-10%, preferably 2-10% or a benzocaine weight percent at least about 1-10%, preferably 2-10%. A method of preparing a composition for forming a protective polymerized film (bandage) after topical application that includes mixing povidone iodine with a buffer solution to form a stock solution (Tables 1, 2, or 3) and combining this solution on a one to one basis with a topical reacting solution (Tables 4, 4-A, 5, 5-A, 6, 6-A, 7, 7-A, 8, 8-A) containing hydroalcoholic benzalkonium chloride, lidocaine or benzocaine is also provided. Stock Solutions (Tables 1, 2 and 3) may contain the commercial preservative GERMABEN II® a registered trademark of International Specialty Products, to inhibit microbial yeast and mold growth, in conjunction with Disodium EDTA, used to prevent crystals from forming in bulk or multi-use packages, especially in tropical and frigid climates. The resulting composition is referred to as ALCODINE®, a solution for topical application which forms a polymerized film (bandage) which provides a sustained release of medicament to the site of application. Thereafter as desired the polymerized film can be removed with cold or warm water and reapplied as needed for further treatment. A related method of treating skin is also disclosed. When the alcohol weight percent of the finished blended solution is between 15-50% local anesthetics such as Lidocaine, Lidocaine HCl, Lidocaine HI, Aspirin, Benzocaine, Dibucaine, Tetracaine, Tetracaine HCL, Tetracaine HI, Trolamine Salicylate, Ethyl Chloride, DMSO, MSM, and others can be utilized individually and/or in combination to reduce short term pain effects of the alcohol on abraded skin wounds and to reduce pain related to the injury or disease being treated. Preferably Lidocaine with a weight percent between 1-12%, preferably 2-10% or Benzocaine with a weight percent between 1-12%, preferably 2-10% are used in this novel formulation for wound pain relief and for pain relief from the effects of alcohol being sprayed in sensitive areas, such as the genitals.

DETAILED DESCRIPTION OF THE PREFERRED EMBODIMENT AND OPERATION OF THE INVENTION

Figure 1:
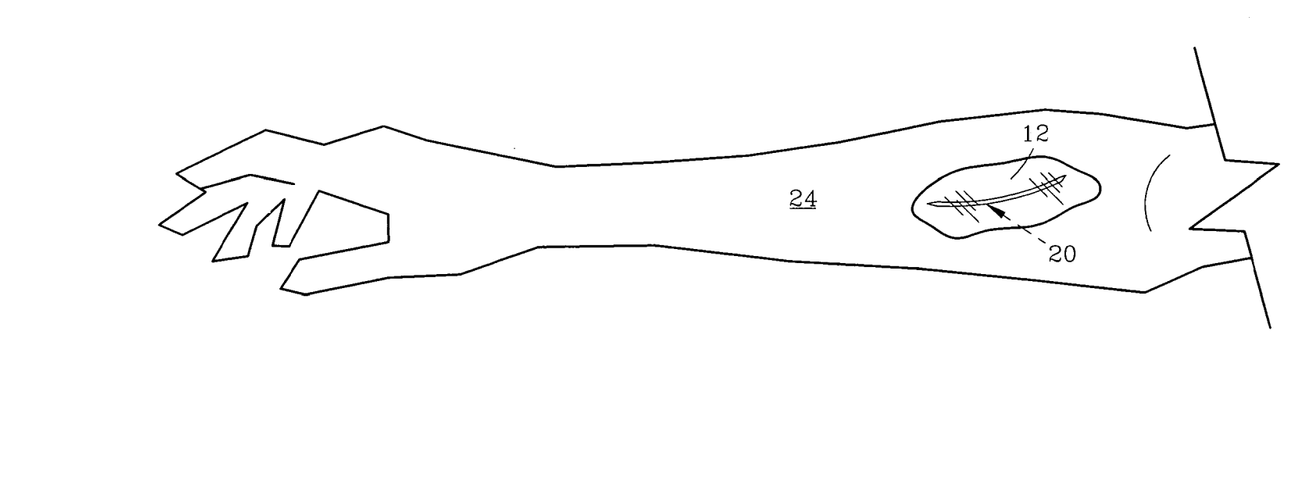
FIG. 1 is a top perspective view of a polymeric film formed by applying a topical composition according to a preferred embodiment of the invention.

For a better understanding of the invention and its operation, turning now to the drawing, FIG. 1 shows a polymeric film 12 formed by applying a topical composition to skin 24 at a minor skin wound or diseased site 20, for example, according to the preferred embodiment of the invention.

The topical composition is formed by combining one of the stock solutions as seen in Tables 1, 2 and 3 below with one of the reacting solutions as seen in Tables 4, 4-A, 5, 5-A, 6, 6-A, 7, 7-A, 8, and 8-A also seen below.

The chemicals used to make the stock solutions are shown below in Tables 1, 2 and 3 with designations corresponding to those provided by the Chemical Abstract Service (CAS). Without being limited thereto, the following illustrates the invention:

TABLE 1

PREFERRED STOCK SOLUTION
Buffered 10% Povidone Iodine Topical Stock Solution:

| Ingredients | Wt. % |
|---|---|
| (1) Purified Water | 86.9335% |
| (2) Citric Acid CAS 77-92-9 | 0.4497% |
| (3) Sodium Phosphate Dibasic CAS 7558-79-4 | 0.5308% |
| (4) Sodium Hydroxide CAS 1310-73-2 | 0.1722% |
| (5) Glycerin CAS 56-81-5 | 0.9569% |
| (6) Nonoxynol-9 CAS 26571-11-9 | 0.9569% |
| (7) Povidone Iodine CAS 25655-41-8 | 10.0000% |
| | 100.0000% |

Although the above concentrations have been optimized for peak efficiency and to avoid undesirable chemical reactions, the following ranges of ingredients are contemplated within the scope of the instant composition: 84-88 Wt.%, preferably 85-87 Wt.% of purified water, 0.3-0.6 Wt.%, preferably 0.4-0.5 Wt.% citric acid, 0.3-0.7 Wt.%, preferably 0.4-0.6 Wt.% sodium phosphate dibasic, 0.05-0.3 Wt.%, preferably 0.1-0.2 Wt.% of sodium hydroxide, 0.8-1.5 Wt.%, preferably 0.9-1.1 Wt.% glycerin, 0.8-1.5 Wt.%, preferably 0.9-1.1 Wt.% of nonoxynol-9, and 9.5-12 Wt. %, preferably 10-11 Wt.% of povidone iodine.

For example, preparation of a one kilogram (1 Kg) batch of buffered 10% Povidone Iodine topical stock solution (Table 1) may be produced as follows:
In a suitable container fitted with a mixer add the ingredients in the order listed while mixing:

| Ingredients | Wt. (g) |
|---|---|
| (1) Purified Water | 869.335 |
| (2) Citric Acid CAS 77-92-9 | 4.497 |
| (3) Sodium Phosphate Dibasic CAS 7558-79-4 | 5.308 |
| (4) Sodium Hydroxide CAS 1310-73-2 | 1.722 |
| (5) Glycerin CAS 56-81-5 | 9.569 |
| (6) Nonoxynol-9 CAS 26571-11-9 | 9.569 |
| (7) Povidone Iodine CAS 25655-41-8 | 100.000 |
| | 1000.000 |

The ingredients listed above are blended in the order listed at 25° C.-30° C. in a suitable container until homogeneous to form the stock solution (Table 1). For sodium sensitive patients, the ingredients Sodium Phosphate Dibasic and Sodium Hydroxide can be substituted with respectively, Potassium Phosphate Dibasic and Potassium Hydroxide.

Blending equal parts of the preferred stock solution (Table 1) above with Hydroalcoholic Benzalkonium Chloride, Lidocaine or Benzocaine (individual or combined embodiments of Tables 4, 4-A, 5, 5-A, 6, 6-A, 7, 7-A, 8, and 8-A), will result in the creation of ALCODINE®, a preferred hydroalcoholic film forming formulation containing at least two (2) in situ formed complexes, Hydroalcoholic Povidone Iodine and Benzalkonium Chloroiodide. For the best administration in the form of a spray, fill the solution into a pump spray bottle. The most preferred pH is 5.5, although a pH between 1.5-6.5 is acceptable. By means of HPLC (High Performance Liquid Chromatography), the ingredients may be monitored and stability of the active ingredients over a long period of time and temperature can be determined. For example, when properly developed, ALCODINE® has a shelf life at room temperature of over five (5) years without loss of efficacy or encountering solubility problems, advantageously contrary to similar observations by other currently available PI solutions.

TABLE 2

FIRST ALTERNATE STOCK SOLUTION
Buffered 10% Povidone Iodine Topical Stock Solution:

| Ingredients | Wt. % |
|---|---|
| (1) Purified Water | 86.9335% |
| (2) Citric Acid CAS 77-92-9 | 0.4497% |
| (3) Sodium Phosphate Dibasic CAS 7558-79-4 | 0.5308% |
| (4) Sodium Hydroxide CAS 1310-73-2 | 0.1722% |
| (5) Glycerin CAS 56-81-5 | 0.9569% |
| (6) MAKON 8 CAS 9016-45-9 | 0.9569% |
| (7) Povidone Iodine CAS 25655-41-8 | 10.0000% |
| | 100.0000% |

Although the concentrations in Table 2 have been optimized for peak efficiency and to avoid undesirable chemical reactions, the following ranges of ingredients are contemplated within the scope of the instant composition: 84-88 Wt.%, preferably 85-87 Wt.% of purified water, 0.3-0.6 Wt.%, preferably 0.4-0.5 Wt.% citric acid, 0.3-0.7 Wt.%, preferably 0.4-0.6 Wt.% sodium phosphate dibasic, 0.05-0.3 Wt.%, preferably 0.1-0.2 Wt.% of sodium hydroxide, 0.8-1.5 Wt.%, preferably 0.9-1.1 Wt.% glycerin, 0.8-1.5 Wt.%, preferably 0.9-1.1 Wt.% of MAKON 8, and 9.5-12 Wt.%, preferably 10-11 Wt.% of povidone iodine.

For example, preparation of a one kilogram (1 Kg) batch of buffered 10% Povidone Iodine topical stock solution (Table 2) may be produced as follows:
In a suitable container fitted with a mixer add the ingredients in the order listed while mixing:

| Ingredients | Wt. (g) |
|---|---|
| (1) Purified Water | 869.335 |
| (2) Citric Acid CAS 77-92-94.497 | |
| (3) Sodium Phosphate Dibasic CAS 7558-79-4 | 5.308 |
| (4) Sodium Hydroxide CAS 1310-73-2 | 1.722 |
| (5) Glycerin CAS 56-81-5 | 9.569 |
| (6) MAKON 8 CAS 9016-45-9 | 9.569 |
| (7) Povidone Iodine CAS 25655-41-8 | 100.000 |
| | 1000.000 |

The ingredients listed above are blended in the order listed at 25° C.-30° C. in a suitable container until homogeneous to form the stock solution (Table 2). For sodium sensitive patients, the ingredients Sodium Phosphate Dibasic and Sodium Hydroxide can be substituted with respectively, Potassium Phosphate Dibasic and Potassium Hydroxide.

Blending equal parts of the stock solution (Table 2) above with Hydroalcoholic Benzalkonium Chloride, Lidocaine or Benzocaine (individual or combined embodiments of Tables 4, 4-A, 5, 5-A, 6, 6-A, 7, 7-A, 8, and 8-A), will result in the creation of ALCODINE®, a preferred hydroalcoholic film forming formulation containing at least two (2) in situ formed complexes, Hydroalcoholic Povidone Iodine and Benzalkonium Chloroiodide. For the best administration in the form of a spray, fill the solution into a pump spray bottle. The most preferred pH is 5.5, although a pH between 1.5-6.5 is acceptable. By means of HPLC, the ingredients may be monitored and stability of the active ingredients over a long period of time and temperature can be determined.

TABLE 3

SECOND ALTERNATE STOCK SOLUTION
Buffered 10% Povidone Iodine Topical Stock Solution:

| Ingredients | Wt. % |
|---|---|
| (1) Purified Water | 87.4643% |
| (2) Citric Acid CAS 77-92-9 | 0.4497% |
| (3) Sodium Hydroxide CAS 1310-73-2 | 0.1722% |
| (4) Glycerin CAS 56-81-5 | 0.9569% |
| (5) MAKON 8 CAS 9016-45-9 | 0.9569% |
| (6) Povidone Iodine CAS 25655-41-8 | 10.0000% |
| | 100.0000% |

Although the concentrations in Table 3 have been optimized for peak efficiency and to avoid undesirable chemical reactions, the following ranges of ingredients are contemplated within the scope of the instant composition: 85-89 Wt.%, preferably 86-88 Wt.% of purified water, 0.3-0.6 Wt.%, preferably 0.4-0.5 Wt.% citric acid, 0.05-0.3 Wt.%, preferably 0.1-0.2 Wt.% of sodium hydroxide, 0.8-1.5 Wt.%, preferably 0.9-1.1 Wt.% glycerin, 0.8-1.5 Wt.%, preferably 0.9-1.1 Wt.% of MAKON 8, and 9.5-12 Wt.%, preferably 10-11 Wt.% of povidone iodine.

For example, preparation of a one kilogram (1 Kg) batch of buffered 10% Povidone Iodine topical stock solution (Table 3) may be produced as follows:
In a suitable container fitted with a mixer add the ingredients in the order listed while mixing:

| Ingredients | Wt. (g) |
|---|---|
| (1) Purified Water | 874.643 |
| (2) Citric Acid CAS 77-92-9 | 4.497 |
| (3) Sodium Hydroxide CAS 1310-73-2 | 1.722 |
| (4) Glycerin CAS 56-81-5 | 9.569 |
| (5) MAKON 8 CAS 9016-45-9 | 9.569 |
| (6) Povidone Iodine CAS 25655-41-8 | 100.000 |
| | 1000.000 |

Blending equal parts of the stock solution (Table 3) above with Hydroalcoholic Benzalkonium Chloride, Lidocaine or Benzocaine (individual or combined embodiments of Tables 4, 4-A, 5, 5-A, 6, 6-A, 7, 7-A, 8, and 8-A), will result in the creation of ALCODINE®, a preferred hydroalcoholic film forming formulation containing at least two (2) in situ formed complexes, Hydroalcoholic Povidone Iodine and Benzalkonium Chloroiodide. For the best administration in the form of a spray, fill the solution into a pump spray bottle. The most preferred pH is 4.5, although a pH between 1.5-6.5 is acceptable. By means of HPLC, the ingredients may be monitored and stability of the active ingredients over a long period of time and temperature can be determined.

Topical Reacting Solutions

In the preferred embodiment of the invention, the reacting solution can be selected from one of the following exothermic reactants:

TABLE 4

PREFERRED TOPICAL REACTING SOLUTION
Ethyl Alcohol Topical Reacting Solution:

| Ingredients | Wt. % |
|---|---|
| (1) Ethyl Alcohol CAS 64-17-5 | 94.87% |
| (2) Benzalkonium Chloride CAS 68424-85-1 | 0.13% |
| (3) Lidocaine CAS 137-58-6 | 5.00% |
| | 100.00% |

The following ranges of ingredients listed in Table 4 are contemplated within the scope of the instant composition: 90-99 Wt.%, preferably 93-95 Wt.% of ethyl alcohol, 0.0005-0.130 Wt.%, preferably 0.125-0.130 Wt.% of benzalkonium chloride, and 1.0-12.0 Wt.%, preferably 2.0-10.0 Wt.% of Lidocaine.

TABLE 4-A

ALTERNATE TOPICAL REACTING SOLUTION
Alternative Embodiment of Ethyl
Alcohol Topical Reacting Solution:

| Ingredients | Wt. % |
|---|---|
| (1) Ethyl Alcohol CAS 64-17-5 | 94.87% |
| (2) Benzalkonium Chloride CAS 68424-85-1 | 0.13% |
| (3) Benzocaine CAS 94-09-7 | 5.00% |
| | 100.00% |

The following ranges of ingredients listed in Table 4-A are contemplated within the scope of the instant composition: 90-99 Wt.%, preferably 93-95 Wt.% of ethyl alcohol, 0.0005-

0.130 Wt.%, preferably 0.125-0.130 Wt.% of benzalkonium chloride, and 1.0-12.0 Wt.%, preferably 2.0-10.0 Wt.% of benzocaine.

For example, preparation of a one kilogram (1 Kg) batch of preferred film forming (Exothermic Reactants) formulation Tables 4, 4-A respectively, may be produced as follows: In a suitable container fitted with a mixer add the ingredients in the order listed while mixing:

| Ingredients | Wt. (g) |
|---|---|
| (1) Ethyl Alcohol CAS 64-17-5 | 948.7 |
| (2) Benzalkonium Chloride CAS 68424-85-1 | 1.3 |
| (3) Lidocaine CAS 137-58-6 | 50.0 |
| | 1000.0 |

Or

| Ingredients | Wt. (g) |
|---|---|
| (1) Ethyl Alcohol CAS 64-17-5 | 948.7 |
| (2) Benzalkonium Chloride CAS 68424-85-1 | 1.3 |
| (3) Benzocaine CAS 94-09-7 | 50.0 |
| | 1000.0 |

The ingredients listed above are blended in the order listed at 25° C.-30° C. in a suitable container until homogeneous to form the topical reacting solutions in Tables 4, 4-A, respectively. Blending equal parts of the preferred stock solution (Table 1) with hydroalcoholic benzalkonium chloride, Lidocaine or benzocaine (Tables 4 or 4-A, respectively) will result in the creation of ALCODINE®, a preferred hydroalcoholic film forming formulation containing at least two (2) in situ formed complexes, hydroalcoholic povidone iodine and benzalkonium chloroiodide. For the best administration in the form of a spray, fill the solution into a pump spray bottle and administer to the affected area, for example a section of damaged dermis. The ingredients may be monitored and stability of the active ingredients over a long period of time and temperature can be determined by means of HPLC.

TABLE 5

ALTERNATE TOPICAL REACTING SOLUTION
Isopropyl Alcohol Topical Reacting Solution:

| Ingredients | Wt. % |
|---|---|
| (1) Isopropyl Alcohol CAS 67-63-1 | 94.87% |
| (2) Benzalkonium Chloride CAS 68424-85-1 | 0.13% |
| (3) Lidocaine CAS 137-58-6 | 5.00% |
| | 100.00% |

The following ranges of ingredients listed in Table 5 are contemplated within the scope of the instant composition: 90-99 Wt.%, preferably 93-95 Wt.% of isopropyl alcohol, 0.0005-0.130 Wt.%, preferably 0.125-0.130 Wt.% of benzalkonium chloride, and 1.0-12.0 Wt.%, preferably 2.0-10.0 Wt.% of Lidocaine.

TABLE 5-A

ALTERNATE TOPICAL REACTING SOLUTION
Alternative Embodiment of Isopropyl
Alcohol Topical Reacting Solution:

| Ingredients | Wt. % |
|---|---|
| (1) Isopropyl Alcohol CAS 67-63-1 | 94.87% |
| (2) Benzalkonium Chloride CAS 68424-85-1 | 0.13% |
| (3) Benzocaine CAS 94-09-7 | 5.00% |
| | 100.00% |

The following ranges of ingredients listed in Table 5-A are contemplated within the scope of the instant composition: 90-99 Wt.%, preferably 93-95 Wt.% of isopropyl alcohol, 0.0005-0.130 Wt.%, preferably 0.125-0.130 Wt.% of benzalkonium chloride, and 1.0-12.0 Wt.%, preferably 2.0-10.0 Wt.% of benzocaine.

For example, preparation of a one kilogram (1 Kg) batch of preferred film forming (Exothermic Reactants) formulation Tables 5 and 5-A may be produced as follows:
In a suitable container fitted with a mixer add the ingredients in the order listed while mixing:

| Ingredients | Wt. (g) |
|---|---|
| (1) Isopropyl Alcohol CAS 67-63-1 | 948.7 |
| (2) Benzalkonium Chloride CAS 68424-85-1 | 1.3 |
| (3) Lidocaine CAS 137-58-6 | 50.0 |
| | 1000.0 |

Or

| Ingredients | Wt. (g) |
|---|---|
| (1) Isopropyl Alcohol CAS 67-63-1 | 948.7 |
| (2) Benzalkonium Chloride CAS 68424-85-1 | 1.3 |
| (3) Benzocaine CAS 94-09-7 | 50.0 |
| | 1000.0 |

The ingredients listed above are blended in the order listed at 25° C.-30° C. in a suitable container until homogeneous to form the topical reacting solution (Tables 5 or 5-A respectively). Blending equal parts of the preferred stock solution (Table 1) with Hydroalcoholic Benzalkonium Chloride, Lidocaine or Benzocaine (Tables 5 or 5-A) will result in the creation of ALCODINE®, a preferred hydroalcoholic film forming formulation containing at least two (2) in situ formed complexes, Hydroalcoholic Povidone Iodine and Benzalkonium Chloroiodide. For the best administration in the form of a spray, fill the solution into a pump spray bottle. By means of HPLC, the ingredients may be monitored and stability of the active ingredients over a long period of time and temperature can be determined.

TABLE 6

ALTERNATE TOPICAL REACTING SOLUTION
Methyl Alcohol Topical Reacting Solution:

| Ingredients | Wt. % |
|---|---|
| (1) Methyl Alcohol CAS 67-56-1 | 94.87% |
| (2) Benzalkonium Chloride CAS 68424-85-1 | 0.13% |
| (3) Lidocaine CAS 137-58-6 | 5.00% |
| | 100.00% |

The following ranges of ingredients listed in Table 6 are contemplated within the scope of the instant composition: 90-99 Wt.%, preferably 93-95 Wt.% of methyl alcohol, 0.0005-0.130 Wt.%, preferably 0.125-0.130 Wt.% of benzalkonium chloride, and 1.0-12.0 Wt.%, preferably 2.0-10.0 Wt.% of Lidocaine.

TABLE 6-A

ALTERNATE TOPICAL REACTING SOLUTION
Alternative Embodiment of Methyl
Alcohol Topical Reacting Solution:

| Ingredients | Wt. % |
| --- | --- |
| (1) Methyl Alcohol CAS 67-56-1 | 94.87% |
| (2) Benzalkonium Chloride CAS 68424-85-1 | 0.13% |
| (3) Benzocaine CAS 94-09-7 | 5.00% |
| | 100.00% |

The following ranges of ingredients listed in Table 6-A are contemplated within the scope of the instant composition: 90-99 Wt.%, preferably 93-95 Wt.% of methyl alcohol, 0.0005-0.130 Wt.%, preferably 0.125-0.130 Wt.% of benzalkonium chloride, and 1.0-12.0 Wt.%, preferably 2.0-10.0 Wt.% of benzocaine.

For example, preparation of a one kilogram (1 Kg) batch of preferred film forming (Exothermic Reactants) formulation Tables 6 or 6-A may be produced as follows:

In a suitable container fitted with a mixer add the ingredients in the order listed while mixing:

| Ingredients | Wt. (g) |
| --- | --- |
| (1) Methyl Alcohol CAS 67-56-1 | 948.7 |
| (2) Benzalkonium Chloride CAS 68424-85-1 | 1.3 |
| (3) Lidocaine CAS 137-58-6 | 50.0 |
| | 1000.0 |

Or

| Ingredients | Wt. (g) |
| --- | --- |
| (1) Methyl Alcohol CAS 67-56-1 | 948.7 |
| (2) Benzalkonium Chloride CAS 68424-85-1 | 1.3 |
| (3) Benzocaine CAS 94-09-7 | 50.0 |
| | 1000.0 |

The ingredients listed above are blended in the order listed at 25° C.-30° C. in a suitable container until homogeneous to form the topical reacting solution (Tables 6 or 6-A respectively). Blending equal parts of the preferred stock solution (Table 1) with Hydroalcoholic Benzalkonium Chloride, Lidocaine or Benzocaine (Tables 6 or 6-A) will result in the creation of ALCODINE®, a preferred hydroalcoholic film forming formulation containing at least two (2) in situ formed complexes, Hydroalcoholic Povidone Iodine and Benzalkonium Chloroiodide. For the best administration in the form of a spray, fill the solution into a pump spray bottle. By means of HPLC, the ingredients may be monitored and stability of the active ingredients over a long period of time and temperature can be determined.

TABLE 7

ALTERNATE TOPICAL REACTING SOLUTION
Butyl Alcohol Topical Reacting Solution:

| Ingredients | Wt. % |
| --- | --- |
| (1) Butyl Alcohol CAS 71-36-3 | 94.87% |
| (2) Benzalkonium Chloride CAS 68424-85-1 | 0.13% |
| (3) Lidocaine CAS 137-58-6 | 5.00% |
| | 100.00% |

The following ranges of ingredients listed in Table 7 are contemplated within the scope of the instant composition: 90-99 Wt.%, preferably 93-95 Wt.% of butyl alcohol, 0.0005-0.130 Wt.%, preferably 0.125-0.130 Wt.% of benzalkonium chloride, and 1.0-12.0 Wt.%, preferably 2.0-10.0 Wt.% of Lidocaine.

TABLE 7-A

ALTERNATE TOPICAL REACTING SOLUTION
Alternative Embodiment of Butyl
Alcohol Topical Reacting Solution:

| Ingredients | Wt. % |
| --- | --- |
| (1) Butyl Alcohol CAS 71-36-3 | 94.87% |
| (2) Benzalkonium Chloride CAS 68424-85-1 | 0.13% |
| (3) Benzocaine CAS 94-09-7 | 5.00% |
| | 100.00% |

The following ranges of ingredients listed as Table 7-A are contemplated within the scope of the instant composition: 90-99 Wt.%, preferably 93-95 Wt.% of butyl alcohol, 0.0005-0.130 Wt.%, preferably 0.125-0.130 Wt.% of benzalkonium chloride, and 1.0-12.0 Wt.%, preferably 2.0-10.0 Wt.% of benzocaine.

For example, preparation of a one kilogram (1 Kg) batch of preferred film forming (Exothermic Reactants) formulation Tables 7 or 7-A may be produced as follows:

In a suitable container fitted with a mixer add the ingredients in the order listed while mixing:

| Ingredients | Wt. (g) |
| --- | --- |
| (1) Butyl Alcohol CAS 71-36-3 | 948.7 |
| (2) Benzalkonium Chloride CAS 68424-85-1 | 1.3 |
| (3) Lidocaine CAS 137-58-6 | 50.0 |
| | 1000.0 |

Or

| Ingredients | Wt. (g) |
| --- | --- |
| (1) Butyl Alcohol CAS 71-36-3 | 948.7 |
| (2) Benzalkonium Chloride CAS 68424-85-1 | 1.3 |
| (3) Benzocaine CAS 94-09-7 | 50.0 |
| | 1000.0 |

The ingredients listed above are blended in the order listed at 25° C.-30° C. in a suitable container until homogeneous to form the topical reacting solution (Tables 7 or 7-A respectively). Blending equal parts of the preferred stock solution (Table 1) with Hydroalcoholic Benzalkonium Chloride, Lidocaine or Benzocaine (Tables 7 or 7-A) will result in the creation of ALCODINE®, a preferred hydroalcoholic film forming formulation containing at least two (2) in situ formed complexes, Hydroalcoholic Povidone Iodine and Benzalkonium Chloroiodide. For the best administration in the form of a spray, fill the solution into a pump spray bottle. By means of HPLC, the ingredients may be monitored and stability of the active ingredients over a long period of time and temperature can be determined.

TABLE 8

ALTERNATE TOPICAL REACTING SOLUTION
Benzyl Alcohol Topical Reacting Solution:

| Ingredients | Wt. % |
| --- | --- |
| (1) Benzyl Alcohol CAS 100-51-6 | 94.87% |
| (2) Benzalkonium Chloride CAS 68424-85-1 | 0.13% |
| (3) Lidocaine CAS 137-58-6 | 5.00% |
| | 100.00% |

The following ranges of ingredients listed in Table 8 are contemplated within the scope of the instant composition: 90-99 Wt.%, preferably 93-95 Wt.% of benzyl alcohol, 0.0005-0.130 Wt.%, preferably 0.125-0.130 Wt.% of benzalkonium chloride, and 1.0-12.0 Wt.%, preferably 2.0-10.0 Wt.% of Lidocaine.

TABLE 8-A

ALTERNATE TOPICAL REACTING SOLUTION
Alternative Embodiment of Topical Reacting Solution:

| Ingredients | Wt. % |
| --- | --- |
| (1) Benzyl Alcohol CAS 100-51-6 | 94.87% |
| (2) Benzalkonium Chloride CAS 68424-85-1 | 0.13% |
| (3) Benzocaine CAS 94-09-7 | 5.00% |
| | 100.00% |

The following ranges of ingredients listed as Table 8-A are contemplated within the scope of the instant composition: 90-99 Wt.%, preferably 93-95 Wt.% of benzyl alcohol, 0.0005-0.130 Wt.%, preferably 0.125-0.130 Wt.% of benzalkonium chloride, and 1.0-12.0 Wt.%, preferably 2.0-10.0 Wt.% of Benzocaine.

For example, preparation of a one kilogram (1 Kg) batch of preferred film forming (Exothermic Reactants) formulation Tables 8 or 8-A may be produced as follows:
In a suitable container fitted with a mixer add the ingredients in the order listed while mixing:

| Ingredients | Wt. (g) |
| --- | --- |
| (1) Benzyl Alcohol CAS 100-51-6 | 948.7 |
| (2) Benzalkonium Chloride CAS 68424-85-1 | 1.3 |
| (3) Lidocaine CAS 137-58-6 | 50.0 |
| | 1000.0 |

Or

| Ingredients | Wt. (g) |
| --- | --- |
| (1) Benzyl Alcohol CAS 100-51-6 | 948.7 |
| (2) Benzalkonium Chloride CAS 68424-85-1 | 1.3 |
| (3) Benzocaine CAS 94-09-7 | 50.0 |
| | 1000.0 |

The ingredients listed above are blended in the order listed at 25° C.-30° C. in a suitable container until homogeneous to form the topical reacting solution (Tables 8 or 8-A respectively). Blending equal parts of the preferred stock solution (Table 1) with Hydroalcoholic Benzalkonium Chloride, Lidocaine or Benzocaine (Tables 8 or 8-A) will result in the creation of ALCODINE®, a preferred hydroalcoholic film forming formulation containing at least two (2) in situ formed complexes, Hydroalcoholic Povidone Iodine and Benzalkonium Chloroiodide. For the best administration in the form of a spray, fill the solution into a pump spray bottle. By means of HPLC, the ingredients may be monitored and stability of the active ingredients over a long period of time and temperature can be determined.

Preferred Film Forming Formulations:
1) Ethyl Povidone Iodine 5% and Benzalkonium Chloride, Lidocaine or Benzocaine: Blend 50 Wt. % Stock Solutions (as seen in Tables 1, 2, or 3); with 50 Wt. % Ethyl Alcohol Reacting Topical Solution (as seen in Tables 4 or 4-A).
2) Isopropyl Povidone Iodine 5% and Benzalkonium Chloride, Lidocaine or Benzocaine: Blend 50 Wt. % Stock Solutions (as seen in Tables 1, 2, or 3); with 50 Wt. % Isopropyl Alcohol Reacting Topical Solution (as seen in Tables 5 or 5-A).
3) Methyl Povidone Iodine 5% and Benzalkonium Chloride, Lidocaine or Benzocaine: Blend 50 Wt. % Stock Solutions (as seen in Tables 1, 2, or 3); with 50 Wt. % Methyl Alcohol Stock Solution (as seen in Tables 6 or 6-A).
4) Butyl Povidone Iodine 5% and Benzalkonium Chloride, Lidocaine or Benzocaine: Blend 50 Wt. % Stock Solutions (as seen in Tables 1, 2, or 3); with 50 Wt. % Butyl Alcohol Reacting Topical Solution (as seen in Tables 7 or 7-A).
5) Benzyl Povidone Iodine 5% and Benzalkonium Chloride, Lidocaine or Benzocaine: Blend 50 Wt. % Stock Solutions (as seen in Tables 1, 2, or 3); with 50 Wt. % Benzyl Alcohol Stock Solution (as seen in Tables 8 or 8-A).

The preferred Ethyl Povidone Iodine with the Benzalkonium Chloroiodide compound is formed in situ in exothermic reactions as follows:
1) Ethyl Povidone Iodine 5% and Benzalkonium Chloroiodide are formed in situ when 50 Wt. % Stock Solutions (as seen in Tables 1, 2, or 3) is blended with 50 Wt. % Ethyl Alcohol Topical Reacting Solutions (as seen in Tables 4 or 4-A).
2) Isopropyl Povidone Iodine 5% and Benzalkonium Chloroiodide are formed in situ when 50 Wt. % Stock Solutions (as seen in Tables 1, 2, or 3) is blended with 50 Wt. % Isopropyl Alcohol Topical Reacting Solutions (as seen in Tables 5 or 5-A).
3) Methyl Povidone Iodine 5% and Benzalkonium Chloroiodide are formed in situ when 50 Wt. % Stock Solutions (as seen in Tables 1, 2, or 3) is blended with 50 Wt. % Methyl Alcohol Topical Reacting Solutions (as seen in Tables 6 or 6-A).
4) Butyl Povidone Iodine 5% and Benzalkonium Chloroiodide are formed in situ when 50 Wt. % Stock Solutions (as seen in Tables 1, 2, or 3) is blended with 50 Wt. % Butyl Alcohol Topical Reacting Solutions (as seen in Tables 7 or 7-A).
5) Benzyl Povidone Iodine 5% and Benzalkonium Chloroiodide are formed in situ when 50 Wt. % Stock Solutions (as seen in Tables 1, 2, or 3) is blended with 50 Wt. % Benzyl Alcohol Topical Reacting Solutions (as seen in Tables 8 or 8-A).

In the preferred embodiments of the invention, the ingredients of the stock solution shown in Table 1 are blended in a suitable container at about twenty-five degrees Celsius (25°

C.) to about thirty degrees Celsius (30° C.) until a homogeneous mixture is achieved. The stock solution is then combined with a hydro-alkane alcohol topical reacting solution including preferably at least about Wt.% 93-95 of either Ethyl Alcohol, Isopropyl Alcohol, Methyl Alcohol, Butyl Alcohol or Benzyl Alcohol and containing benzalkonium chloride Wt.% 0.005-0.130%, preferably 0.125-0.130%, lidocaine Wt.% at least about 1-12%, preferably 2-10% or benzocaine Wt.% at least about 1-12%, preferably 2-10%, at a ratio of about equal weight percent stock solution (Tables 1, 2, or 3) and hydroalcoholic topical reacting solutions (Tables 4, 4-A, 5, 5-A, 6, 6-A, 7, 7-A, 8, or 8-A) producing exothermic chemical reactions, from which the water soluble polymeric film forming topical compositions results.

Also, while in the preferred embodiment, povidone iodine constitutes about Wt. % 10, preferably 10-11% of the total of the buffered stock and alcoholic solutions prior to their combination, the relative amounts of the two solutions to be combined can be adjusted to provide povidone iodine at from about Wt. % 2-10% of the total of the two solutions prior to their combination. Similarly, adjusting the amount of povidone iodine in the stock solution before combining it with the selected alcoholic solution can produce the same ratios of povidone iodine. Such adjustments would also change the relative amounts of the other ingredients present in the solutions. It may also be possible to exclude or adjust the amount of one or more of the citric acid, sodium phosphate dibasic, sodium hydroxide, glycerin, nonoxynol-9, or MAKON 8 in the stock solution and still produce an effective topical composition. However, the specific ratio of active ingredients is particularly important, specifically with respect to the benzalkonium chloride which should not be blended at a higher concentration due to solubility issues. Based on laboratory experimentation, solutions formed as described in Example 1 below with greater than 0.13% Benzalkonium Chloride cause the ingredient to "crash out" and render the solution useless.

Example 1

A stock solution of buffered povidone iodine is prepared by blending the ingredients listed in either Tables 1, 2 or 3 above in a suitable container at about twenty-five degrees Celsius (25° C.) to about thirty degrees Celsius (30° C.) until homogeneous. Next, blend equal parts of the selected buffered povidone iodine stock solution (from Tables 1, 2 or 3) with Alcohol Wt.% 90-99, preferably 93-95 Wt.%, Benzalkonium Chloride Wt.% 0.005-0.130%, preferably 0.125-0.130%, lidocaine Wt.% at least about 1-12%, preferably 2-10% or benzocaine Wt.% at least about 1-12%, preferably 2-10%, topical reacting solution to produce an exothermic reaction. The buffered povidone iodine solution is pre-mixed to prevent the release of noxious chemical ingredients which occur if the ingredients of the buffered solution and the reacting solution are all mixed together at the same time. The resulting stable composition is then applied to the skin by spraying or wiping at the abrasion, laceration or diseased site, where a protective polymeric film (bandage) develops which will provide protection to the applied area while supplying a sustained release of medicament to treat and heal the abrasion, laceration or diseased condition. As would be understood when in use should the alcohol content of the finished blended solution be between fifteen Wt.% 15-50%, local anesthetics such as Lidocaine, Lidocaine HCl, Lidocaine HI, Aspirin, Benzocaine, Dibucaine, Tetracaine, Tetracaine HCL, Tetracaine HI, Trolamine Salicylate, Ethyl Chloride, DMSO, MSM, and others can be utilized individually and/or in combination to reduce short term pain effects of the alcohol on abraded skin wounds, while also reducing the pain associated with the abrasion, laceration or diseased condition. Thereafter, the protective film can be removed using cold or warm water if desired. A re-application can be made as necessary until the healing is complete.

Other film forming hydroalcoholic Povidone Iodine Solution concentrations of 2%, 3%, 7% and 10% can be formed by blending an appropriate amount of stock solution from either Tables 1, 2 or 3 with an appropriate amount of Hydroalcoholic benzalkonium chloride (Wt. % 0.005%-0.130%), lidocaine (Wt. % 1%-12%) or benzocaine (Wt. % 1%-12%), topical reacting solution or by adjusting upward the amount of povidone iodine in the 10% product. The stock solution can also be prepared including or excluding Sodium Phosphate Dibasic in combination with MAKON 8 in Tables 2 and 3, which is substituted for nonoxynol-9 in Table 1. These products are also readily adaptable for spray on applications.

Benzalkonium chloride is an essential ingredient of the instant invention, because it maximizes the safe and effective killing power of the solutions described herein against many bacteria, fungi and viruses. However, at room temperature it loses solubility in solution above 0.13%, rendering the resulting mixture useless as an effective antimicrobial agent.

The Ethyl Povidone Iodine 5% and Benzalkonium Chloroiodide with Lidocaine or Benzocaine solution is the preferred form of the product for effective emergency iodine therapy to protect the thyroid gland after radiation exposure. Further the Ethyl Povidone Iodine 5% and Benzalkonium Chloroiodide with Lidocaine or Benzocaine solution may also be used as directed by a Physician, Dentist, Pharmacist or other health care official as an oral spray to treat gum diseases, tooth decay, to help alleviate tooth ache pain, throat soreness, nasal and oral cavity congestion.

The Hydroalcoholic Povidone Iodine and Benzalkonium Chloroiodide with Lidocaine or Benzocaine complexes developed in combination in situ in the instant invention represent the first claimed use of such medicaments in treating and curing severe topical skin cases of MRSA, cellulitis, athletes' feet, jock itch, bed sores, acne, blemishes, full body cleansing and maintenance, body deodorant, PFB's (Pseudo-Folliculittis Barbae), cold sores, herpes simplex and many other skin conditions and diseases as well as sanitizing commercial production machinery and water purification. The formulations can also be utilized for controlling dog mange, flea and tick conditions and treatment of fish aquariums. Further the Hydroalcoholic Povidone Iodine and Benzalkonium Chloroiodide with Lidocaine or Benzocaine complexes are also effective in unit dose packages for emergency iodine therapy to protect the thyroid gland after radiation exposure.

The unique combination of ingredients in the finished blended solutions of the instant invention are stable at ambient temperatures and do not freeze as do other prior art formulations. Further the film forming solutions when sprayed onto the injured, infected or otherwise diseased skin quickly dry to the touch and are interactive with body fluids and mucosa to provide a sustained release of medicaments. The formulations described herein provide a sustained release of hydroalcoholic povidone iodine and hydroalcoholic benzalkonium chloroiodide in a stable polymerized povidone iodine film which is water soluble.

Product Invitro Testing

Michael C. Hudson, PhD, Professor of Biology, The University of North Carolina at Charlotte, 9201 University City Blvd., Charlotte, N.C. 28223, tested two (2) versions of our Hydroalcoholic Povidone Iodine Solution, (ALCODINE®):

(A) containing 0.0 Wt.% Benzalkonium Chloride and (B) containing 0.130 Wt.% Benzalkonium Chloride. He focused his testing at the inventor's request upon the effectiveness of our compositions ALCODINE® compared to the product commercially available under the trade name BETADINE® against two (2) Gram-positive organisms of Methacillin-resistant *Staphylococcus aureus*, Community Acquired MRSA (CA-MRSA) and Hospital Acquired MRSA (HA-MRSA).

Following the testing, he reported that the Hydroalcoholic Povidone Iodine Solution, (ALCODINE®) (A) containing 0.0 Wt.% Benzalkonium Chloride was 25% more effective than BETADINE® and (B) containing 0.130 Wt.% Benzalkonium Chloride was 50% more effective than BETADINE®.

Using our Hydroalcoholic Povidone Iodine Solution, (ALCODINE®) Dr. Hudson also performed tests as outlined in the in vitro MIC section of 21 CFR 333.470 according to FDA GMP requirements against twenty-six (26) non-clinical strains of bacteria to establish whether it possesses acceptable levels of antimicrobial efficacy to be used as a topical antiseptic. The twenty-six (26) non-clinical strains were as follows:

Gram-negative organisms:
  i. *Acinetobacter* sp.
  ii. *Bacteroides fragilis*
  iii. *Haemophilus* influenza
  iv. *Enterobacter* sp.
  v. *Escherichia coli* ATCC 11229
  vi. *Escherichia coli* ATCC 25922
  vii. *Klebsiella* sp.
  viii. *Klebsiella pneumonia*
  ix. *Pseudomonas aeruginosa* ATCC 15442
  x. *Pseudomonas aeruginosa* ATCC 27853
  xi. *Proteus mirabilis*
  xii. *Serratia marcascens* ATCC 14756

Gram-positive organisms:
  i. *Staphylococcus aureus* ATCC 6538
  ii. *Staphylococcus aureus* ATCC 29213
  iii. *Staphylococcus epidermidis* ATCC 12228
  iv. *Staphylococcus hominis*
  v. *Staphylococcus haemolyticus*
  vi. *Staphylococcus saprophyticus*
  vii. *Micrococcus luteus* ATCC 7468
  viii. *Streptococcus pyogenes*
  ix. *Enterococcus faecalis* ATCC 29212
  x. *Enterococcus faecium*
  xi. *Streptococcus pneumoniae*
  xii. Methacillin-resistant *Staphylococcus aureus*

Yeast:
  i. *Candida* sp.
  ii. *Candida albicans*

The Hydroalcoholic Povidone Iodine Solution, (ALCODINE®) (B) containing 0.130 Wt. % Benzalkonium Chloride was shown to be superior to BETADINE® in effectiveness in containing and destroying the test organisms used in the study.

Thirty (30) people between 12-90 years of age who presented to physicians and had confirmed that their skin lesions were indeed manifestations of MRSA Infections were designated as test subjects. These patients were not being healed by standard medical treatments. Each of these individuals was given a two (2) fl oz pump spray bottle of Hydroalcoholic Povidone Iodine Solution, (ALCODINE®) (B) containing 0.130 Wt. % Benzalkonium Chloride along with the following instructions:

ALCODINE® SEALS SKIN WOUNDS WITH A STERILE IODINE FILM WHICH ACTIVATES AND ASSISTS THE BODY'S NATURAL HEALING PROCESSES. SUCCESSFUL USES FOR ALCODINE®

The following are a few examples of suggested use for the instant invention:

Many MRSA wounds present in a weeping condition because of infections. Such wounds should be pre-cleaned or irrigated with a sterile fluid such as USP 3% Hydrogen Peroxide before spraying or applying ALCODINE® directly onto the area of the wound to seal and protect the wound. Repeat this procedure daily until the wound is completely healed. Applying ALCODINE® frequently as needed will promote rapid healing.

ALCODINE® should be used by all who have limited bath water resources (i.e. campers, the military, and third world individuals). Spray or apply ALCODINE® directly onto all parts of the body including the closed eyes lids (NOT DIRECTLY INTO THE EYES), the underarms, groin areas, and feet to prevent body odor and infections. Apply ALCODINE® frequently as needed to remain odor free. The dried ALCODINE® film won't rub off but is easily removed or rinsed off with cold or warm water.

ALCODINE® can be used to promptly kill germs in minor cuts, burns, scrapes, and minor skin wounds. Apply ALCODINE® directly onto properly prepared minor cuts, burns, scrapes, and minor skin wounds. Applying ALCODINE® frequently as needed will control and destroy germs, prevent infections and promote rapid healing of minor cuts, burns, scrapes, and minor skin wounds.

Spray or apply ALCODINE® directly onto feet and between toes to contain, control and cure the fungus infection which causes foot irritation. Applying ALCODINE® frequently as needed will keep feet and toes healthy and odor free.

Spray or apply ALCODINE® directly onto the groin area including the genitals to contain and cure the condition known as "jock itch" and to eliminate pain and odor. Applying ALCODINE® frequently as needed to remain free of this condition.

Spray or apply ALCODINE® directly onto facial bumps and blemishes preferably at night for the best results. Applying ALCODINE® frequently as needed will control and eliminate facial bumps and blemishes.

Many wounds known as bed sores present in a weeping condition because of infections. Such wounds should be pre-cleaned or irrigated with a sterile fluid such as USP 3% Hydrogen Peroxide before spraying or applying ALCODINE® directly onto the area of the wound to seal and protect the wound. Repeat this procedure daily until the wound is completely healed. Applying ALCODINE® frequently as needed will promote rapid healing of this condition.

PFB'S (Pseudo-Folliculitis Barbae) is a skin condition generally associated with shaving and bumping. Apply ALCODINE® directly onto the area of the face and beard, preferably overnight to destroy the bacteria on the face. Use BETTER SHAVE® Shaving Cream as a Pre and Post Shaving Conditioner to help contain and correct this condition. Apply ALCODINE® frequently at night as needed to promote rapid healing of this condition.

Spray or apply ALCODINE® directly onto the area of the sting or bug bite to help reduce irritation, swelling and pain. Apply ALCODINE® frequently as needed to promote rapid healing.

Hydroalcoholic Povidone Iodine Solution, (ALCODINE®) (B) containing 0.130 Wt. % of Benzalkonium Chloride has been tested as a treatment for facial bumps, bruises, scrapes fungal irritations, and insect bites and found its curative properties to be outstanding. When the product was sprayed onto body surfaces, a sustained releasing Iodine film was formed. This product has been consistently evaluated since 1999 and has found to be very stable and will not freeze. No negative side effects have been observed to date when used on all external surfaces of the body, excluding the eyes.

The instant disclosure for Hydroalcoholic Povidone Iodine Solution, (ALCODINE®) (B) containing 0.130% Wt.% Benzalkonium Chloride (ALCODINE®) contains formulations combining ingredients which permit free Iodine, slowly liberated from the Povidone Iodine (PI) in the Hydroalcoholic Complex of Benzalkonium Chloroiodide in the polymeric solution, "to kill Eukaryotic or Prokaryotic Cells through Iodination of lipids and oxidation of cytoplasmic and membrane compounds". The combination of agents in ALCODINE® exhibits a broad range of antimicrobicidal activity against bacteria, fungi, protozoa and viruses. Slow release of Iodine from the PI Complex in solution minimizes Iodine Toxicity towards Mammalian Cells.

The illustrations and examples provided herein are for explanatory purposes and are not provided to limit the scope of the appended claims.

We claim:

1. A microbicidal buffered hydroalcoholic povidone iodine composition comprising:
    a buffered stock solution formed from 87% by weight purified water, 0.4% by weight granular citric acid, 0.5% by weight granular sodium phosphate dibasic, 0.1% by weight sodium hydroxide, 0.9% by weight glycerin, 0.9% by weight nonoxynol-9, and 10% by weight granular povidone iodine; and
    a reacting solution formed from 94% by weight alcohol, 5% by weight anesthetic, and no more than 0.13% by weight benzalkonium chloride,
    wherein the buffered stock solution and the reacting solution are combined in a stable solution having between 15-50% by weight alcohol content by mixing equal parts by weight the stock solution with the reacting solution to produce an exothermic reaction, and
    wherein a protective polymerized film configured for the sustained release of medicament forms when the stable solution is applied to the site of an injury.

2. The composition of claim 1 wherein the reacting solution further comprises ethyl alcohol in a range of 93-95% by weight and benzalkonium chloride in a range of 0.0005-0.130% by weight.

3. The composition of claim 1 wherein the reacting solution further comprises isopropyl alcohol in a range of 93-95% by weight and benzalkonium chloride in a range of 0.0005-0.130% by weight.

4. The composition of claim 1 wherein the reacting solution further comprises methyl alcohol in a range of 93-95% by weight and benzalkonium chloride in a range of 0.0005-0.130% by weight.

5. The composition of claim 1 wherein the reacting solution further comprises butyl alcohol in a range of 93-95% by weight and benzalkonium chloride in a range of 0.0005-0.130% by weight.

6. The composition of claim 1 wherein the reacting solution further comprises benzyl alcohol in a range of 93-95% by weight and benzalkonium chloride in a range of 0.0005-0.130% by weight.

7. A method of treating injured skin with a microbicidal buffered hydroalcoholic povidone iodine composition comprising the steps of:
    a) preparing a buffered stock solution at about 25° C.-30° C. containing povidone iodine comprised of 87% by weight purified water, 0.4% by weight granular citric acid, 0.5% by weight granular sodium phosphate dibasic, 0.1% by weight sodium hydroxide, 0.9% by weight glycerin, 0.9% by weight nonoxynol-9, and 10% by weight granular povidone iodine;
    b) preparing a reacting solution containing a hydroalcoholic benzalkonium chloride including benzalkonium chloride in a range of 0.0005-0.130% by weight;
    c) forming a stable solution having between 15-50% by weight alcohol content by mixing about equal parts by weight the stock solution with the reacting solution to produce an exothermic reaction;
    d) utilizing a local anesthetic selected from the group consisting of Lidocaine, Lidocaine HCl, Lidocaine HI, Aspirin, Benzocaine, Dibucaine, Tetracaine, Tetracaine HCL, Tetracaine HI, Trolamine Salicylate, Ethyl Chloride, DMSO, and MSM, to reduce short term pain caused by said stable solution;
    e) applying the stable solution onto the injured skin;
    f) leaving the stable solution on the injured skin while a protective polymerized film develops;
    g) releasing medicament from the film to the injured skin; and
    h) sustaining the release of medicament from the film while the injured skin is healing.

8. The method of claim 7 wherein forming a stable solution further comprises the steps of providing ethyl alcohol in a range of 93-95% by weight of the reacting solution and forming ethyl povidone iodine and benzalkonium chloroiodide in an in situ exothermic reaction.

9. The method of claim 7 wherein forming a stable solution further comprises the steps of providing isopropyl alcohol in a range of 93-95% by weight of the reacting solution and forming isopropyl povidone iodine and benzalkonium chloroiodide in an in situ exothermic reaction.

10. The method of claim 7 wherein forming a stable solution further comprises the steps of providing methyl alcohol in a range of 93-95% by weight of the reacting solution and forming methyl povidone iodine and benzalkonium chloroiodide in an in situ exothermic reaction.

11. The method of claim 7 wherein forming a stable solution further comprises the steps of providing butyl alcohol in a range of 93-95% by weight of the reacting solution and forming butyl povidone iodine and benzalkonium chloroiodide in an in situ exothermic reaction.

12. The method of claim 7 wherein forming a stable solution further comprising the steps of providing benzyl alcohol in a range of 93-95% by weight of the reacting solution and forming benzyl povidone iodine and benzalkonium chloroiodide.

13. The method of claim 7 further comprising the step of adding a first preservative to the stock solution to inhibit microbial yeast and mold growth.

14. The method of claim 13 further comprising the step of adding a second preservative to the stock solution to prevent crystal formation.

* * * * *